(12) United States Patent
Lee et al.

(10) Patent No.: US 9,757,319 B2
(45) Date of Patent: Sep. 12, 2017

(54) PRODUCING METHOD OF COSMETICS COMPOSITION FOR A LIP TATTOO PACK AND THEREFROM

(71) Applicant: NEW & NEW CO., LTD., Cheonan, Chungcheongnam-Do (KR)

(72) Inventors: Ho Young Lee, Chungcheongnam-Do (KR); Gun Ho Lee, Seoul (KR); Seong Yong Kim, Chungcheongnam-Do (KR); Ok Jin Joung, Chungcheongnam-Do (KR); Min Jin Cha, Chungcheongnam-Do (KR); Mi Mi Park, Chungcheongnam-Do (KR); Young Im Shin, Chungcheongnam-Do (KR); So Yeon Lee, Chungcheongnam-Do (KR)

(73) Assignee: New & New Co., Ltd, Cheonan, Chungcheongnam-Do (KR)

( * ) Notice: Subject to any disclaimer, the term of this patent is extended or adjusted under 35 U.S.C. 154(b) by 0 days.

(21) Appl. No.: 14/947,118

(22) Filed: Nov. 20, 2015

(65) Prior Publication Data

US 2016/0074299 A1    Mar. 17, 2016

Related U.S. Application Data

(63) Continuation of application No. 14/546,679, filed on Nov. 18, 2014, now abandoned, which is a continuation of application No. PCT/KR2014/005867, filed on Jul. 1, 2014.

(30) Foreign Application Priority Data

Nov. 28, 2013 (KR) .................. 10-2013-0145894
Nov. 28, 2013 (KR) .................. 10-2013-0145895

(51) Int. Cl.
| | | |
|---|---|---|
| A61K 8/34 | (2006.01) | |
| A61K 8/63 | (2006.01) | |
| A61Q 1/06 | (2006.01) | |
| A61K 8/49 | (2006.01) | |
| A61Q 1/02 | (2006.01) | |
| A61K 8/365 | (2006.01) | |
| A61K 8/81 | (2006.01) | |
| A61Q 19/00 | (2006.01) | |
| A61K 8/04 | (2006.01) | |
| A61K 8/60 | (2006.01) | |

(52) U.S. Cl.
CPC ............ *A61K 8/4946* (2013.01); *A61K 8/042* (2013.01); *A61K 8/34* (2013.01); *A61K 8/345* (2013.01); *A61K 8/365* (2013.01); *A61K 8/498* (2013.01); *A61K 8/602* (2013.01); *A61K 8/63* (2013.01); *A61K 8/8129* (2013.01); *A61Q 1/025* (2013.01); *A61Q 1/06* (2013.01); *A61Q 19/007* (2013.01); *A61K 2800/43* (2013.01); *A61K 2800/596* (2013.01); *A61K 2800/74* (2013.01); *A61K 2800/805* (2013.01)

(58) Field of Classification Search
None
See application file for complete search history.

(56) References Cited

U.S. PATENT DOCUMENTS

2009/0263660 A1* 10/2009 Takeuchi ................. A61K 8/44
                                                                428/407

* cited by examiner

*Primary Examiner* — David J Blanchard
*Assistant Examiner* — Sarah Chickos
(74) *Attorney, Agent, or Firm* — Mintz Levin Cohn Ferris Glovsky and Popeo, P.C.; Kongsik Kim; Linyu Mitra

(57) ABSTRACT

Disclosed is a cosmetic composition spread on lips to provide a color to lips. Disclosed are a lip pack cosmetic composition for tattooing and a method of preparing the same wherein lips are pigmented and thereby have tattoo effects by removing a formed layer after pigmenting a color on lips and drying the pigmented lips.

5 Claims, 8 Drawing Sheets

PRODUCING METHOD OF COSMETICS COMPOSITION FOR A LIP TATTOO PACK AND THEREFROM

CROSS-REFERENCE TO RELATED APPLICATIONS

This is a continuation of U.S. application Ser. No. 14/546,679 filed on Nov. 18, 2014, which is a continuation of International Application No. PCT/KR2014/005867 filed on Jul. 1, 2014, which claims priority to Korean Application No 10-2013-0145894 filed on Nov. 28, 2013 and Korean Application No. 10-2013-0145895 filed on Nov. 28, 2013. The applications are incorporated herein by reference.

TECHNICAL FIELD

The present invention relates to a lip pack cosmetic composition for tattooing and a method of preparing the same. More particularly, the present invention relates to a lip pack cosmetic composition for tattooing and a method of preparing the same wherein a thin layer is formed by drying after spreading lips, lips from which the formed layer is removed are pigmented and a color may be maintained for a long time.

BACKGROUND ART

Cosmetics are classified into various types according to application parts, purposes of use, or constituting elements and types of products. For example, cosmetics may be classified into basic cosmetics (skin care cosmetics), makeup cosmetics (color cosmetics), body care cosmetics (body cleansing cosmetics), hair care cosmetics, cosmetics for a mouth, aromatic cosmetics and the like. Makeup cosmetics are used to make a beautiful skin color and to cover blemishes which are not covered with basic cosmetics by providing colors on a body such as a face, nails and the like after using basic cosmetics. Makeup cosmetics are classified into base makeup and point makeup. Base makeup is used to healthily and beautifully trim a skin uniformly by making a skin color of a full face and by covering blemishes such as stains, freckles and the like. Point makeup is used to naturally express individuality by partially emphasizing colors on lips, eyes, cheeks, nails or the like, or by providing a three-dimensional effect through shading. As point makeup, there are lipsticks, cheek blusher (rouge), eye shadow, eyeliners, nail polish and the like.

Among the point makeup, lipsticks are excellent cosmetics to express individuality. Lipsticks are used to provide color and gloss when applied to the lips. An additional purpose of lipsticks is to protect lips from cold, drying and the like. Generally, lipsticks are prepared into a soft stick having good elasticity by dispersing or dissolving color additives in an emulsion. In this case, as desired, fragrances, antioxidants, preservatives and the like may be added to lipsticks.

However, conventional lipsticks easily are smeared on foods or containers contacted with lips or removed and thereby lipsticks are continuously re-applied. In addition, when lipsticks are continuously re-applied, dead skin cells accumulate on lips and thereby lips looks messy. Accordingly, to solve the problems, Korean Patent Application Pub. No. 10-1996-0040344 (Lip Cosmetic Composition Having Persistence), Korean Patent No. 0152554 (Lip Cosmetic Composition), and Korean Patent Application Pub. No. 91-003078 (Lipstick Composition Not Smeared On Lips) proposed technologies to enhance persistency of lipsticks. However, prior technologies are not suitable for maintaining a color of a lipstick for 5 hours or more.

Recently, lip tattoo stickers providing a variety of colors and patterns on lips, and transient tattoo effects are popular. The lip tattoo stickers have superior persistency. However, the lip tattoo stickers are harmful to the human body due to adhesives used to provide a variety of colors on lips and, by using the lip tattoo stickers, lips may be easily dried.

Accordingly, inventors of the present invention studied about a lip pack cosmetic composition for tattooing which is harmless to the human body, and continuously provides a color on lips and, at the same time, sufficient moisture, thus completing the present invention.

SUMMARY

Therefore, the present invention has been made in view of the above problems, and it is an object of the present invention to provide a lip pack cosmetic composition for tattooing so as to provide transient tattoo effects due to excellent color persistency.

Another object of the present invention is to provide a lip pack cosmetic composition for tattooing so as to pigment lips not using oil based raw materials.

A further object of the present invention is to provide a lip pack cosmetic composition for tattooing so as to provide a color to lips and, at the same time, sufficient moisture such that lips are not dried.

A further object of the present invention is to provide a method of preparing a lip pack cosmetic composition for tattooing so as to provide a clear color on lips and transient tattoo effects due to excellent color persistency.

A further object of the present invention is to provide a method of preparing a lip pack cosmetic composition for tattooing so as to provide a clear color on lips and, at the same time, sufficient moisture such that lips are not dried.

In accordance with an aspect of the present invention, the above and other objects can be accomplished by the provision of a cosmetic composition being spread on lips and providing a color so as to pigment and provide tattoo effects by removing a formed layer after spreading and drying the cosmetic composition on lips.

In accordance with another aspect of the present invention, there is provided a lip pack cosmetic composition for tattooing wherein a color pigmented on lips is maintained for 12 hours or more.

In accordance with another aspect of the present invention, there is provided a lip pack cosmetic composition for tattooing wherein a color pigmented on lips is slowly lost as time passes when a predetermined time is over.

The lip pack cosmetic composition for tattooing of the present invention spread on lips provides a color and moisture elements on lips. Especially, the lip pack cosmetic composition for tattooing of the present invention may pigment lips and thus may be used as a product for lip tattooing. In particular, the lip pack cosmetic composition for tattooing of the present invention spread on lips in a proper amount forms a thin layer (film) after a certain time. After completely drying the formed thin layer, the dried thin layer is slowly removed from lips. As a result, lip are pigmented the pigmented color may be maintained for 12 hours or more. In addition, since the lip pack cosmetic composition for tattooing of the present invention does not use oil based raw materials, the lip pack cosmetic composition is a water-soluble composition. Therefore, to remove a color on lips, separate cleansing is not required and, as a certain time passes, the color may be naturally lost though general washing. Furthermore, the lip pack cosmetic composition for tattooing of the present invention may provide sufficient moisture on lips and effectively prevent lips to be dried due to pigmentation.

Preferably, the lip pack cosmetic composition for tattooing of the present invention may include polyvinyl alcohol, a coloring pigment, ethanol, an organic acid and distilled water, more particularly at least one skin moisturizer selected from the group consisting of allantoin, dipotassium glycyrrhizate and butylene glycol, polyvinyl alcohol, a coloring pigment, ethanol, an organic acid, fragrances and distilled water.

The present invention uses distilled water as a solvent. By using distilled water as a solvent, a water-soluble lip pack cosmetic composition may be provided. Conventional lipsticks or lip glosses are oil based compositions using wax or oil as solvents. However, the lip pack cosmetic composition for tattooing of the present invention is an aqueous composition using distilled water as a solvent.

In addition, the present invention is characterized by including polyvinyl alcohol. Here, polyvinyl alcohol functions as a water-soluble film forming agent. Accordingly, after spreading the lip pack cosmetic composition for tattooing of the present invention on lips and then waiting for a certain time, a thin layer may be formed. For example, after spreading the lip pack composition for tattooing of the present invention on lips and then waiting for approximately 10 to 15 minutes, the composition is completely dried. Here, a formed layer may be easily removed by hand.

In addition, the present invention preferably includes a coloring pigment, more particularly a dye, which is changed into a metal compound type, insoluble in water. For example, the coloring pigment may be a lake pigment. By including the lake pigment in the present invention, a clear color and excellent coloring may be provided to lips. Here, a color of the lake pigment is not specifically limited and a variety of colors may be selectively used.

In addition, the present invention preferably includes ethanol and does not use wax or oil used in the conventional lipsticks or lip glosses.

In addition, the present invention is characterized by including an organic acid. The present invention may include at least one selected from the group consisting of citric acid, malic acid, tartaric acid and lactic acid. By including the organic acid, nutrients and moisture elements may further be provided to lips and thereby lips become more moist and glossy. In addition, a color may be pigmented to lips and persistency and coloring of the color may be improved. Here, as an organic acid used in the present invention, an organic acid which is not a salt type is preferable.

In addition, the present invention preferably includes at least one skin moisturizer selected from the group consisting of allantoin, dipotassium glycyrrhizate and butylene glycol. By using the skin moisturizer, sufficient moisture may be provided to lips, and moist and glossy lips may be expressed by removing dead skin cells.

In addition, the present invention includes preferably a fragrance. Here, the fragrance, which is not specifically limited, may be a fragrance element conventionally used in the art fields of the present invention. The fragrance may be preferably a water-soluble fragrance.

In addition, the lip pack cosmetic composition for tattooing of the present invention preferably may include 0.01 to 0.10 wt % of allantoin, 0.01 to 0.10 wt % of dipotassium glycyrrhizate, 0.5 to 1.0 wt % of butylene glycol, 15.0 to 30.0 wt % of polyvinyl alcohol, 0.01 to 0.20 wt % of a coloring pigment, 1.0 to 5.0% of ethanol (alcohol), 0.1 to 2.0 wt % of an organic acid, 0.05 to 0.50% of a fragrance, and 65.0 to 80.0 wt % of distilled water. When the present invention includes each of the above components, lips may be efficiently pigmented and, at the same time, the lips may be sufficiently moisture. Accordingly, moist and glossy lips may be expressed.

In addition, a formulation of the lip pack cosmetic composition for tattooing of the present invention, which is not specifically limited, is preferably a gel type. By using the gel type composition, it is easy to spread the composition on lips in a proper amount and the composition is dried within a short time and formed to a thin layer. In addition, the formed layer may be easily removed.

Meanwhile, the method of preparing the lip pack cosmetic composition for tattooing of the present invention includes (A) cooling at 40 to 50° after adding polyvinyl alcohol to distilled water; (B) cooling at 25 to 35° C. after adding a mixture of a coloring pigment, ethanol and an organic acid thereto; and (C) adjusting pH to 3.0 to 5.5 by adding an organic acid thereto.

Hereinafter, each step of the method of preparing the lip pack cosmetic composition for tattooing of the present invention will be described in detail.

[(A) Cooling at 40 to 50° C. After Adding Polyvinyl Alcohol to Distilled Water]

This step is a cooling step at 40 to 50° C. after adding polyvinyl alcohol to distilled water. Here, when polyvinyl alcohol is added to distilled water, it is preferable to adjust a temperature of distilled water to 80±3° C. In this case, polyvinyl alcohol may be completely dissolved in distilled water. After completely dissolving polyvinyl alcohol, it is preferable to cool to 40 to 50° C.

The present invention uses distilled water as a solvent. By using distilled water as a solvent, a water-soluble lip pack cosmetic composition may be provided. Conventional lipsticks or lip glosses are oil based compositions using wax or oil as a solvent. However, the lip pack cosmetic composition for tattooing of the present invention is an aqueous composition using distilled water as a solvent.

In the present invention, polyvinyl alcohol is added to distilled water. Here, polyvinyl alcohol functions as a water-soluble film forming agent. Accordingly, after spreading the lip pack cosmetic composition for tattooing of the present invention on lips and waiting for a certain time, the composition is dried while forming a thin layer. For example, after spreading the lip pack composition for tattooing of the present invention on lips and waiting for approximately 10 to 15 minutes, the composition is completely dried. Here, a formed layer may be easily removed from lips by hand.

Meanwhile, before adding polyvinyl alcohol to distilled water, it is preferable to dissolving at least one skin moisturizer selected from the group consisting of allantoin, dipotassium glycyrrhizate and butylene glycol in distilled water in advance. By dissolving a moisturizer in distilled water in advance, sufficient moisture may be provided to the lips and moist and glossy lips may be expressed by removing dead skin cells.

[(B) Cooling at 25 to 35° C. After Adding Mixture of Coloring Pigment, Ethanol and Organic Acid Thereto]

This step is a step adding a mixture a coloring pigment, ethanol and an organic acid uniformly stirred in advance to the mixture of step (A) and then re-cooling at 25 to 35° C., after the cooling of step (A).

In the present invention, a coloring pigment, ethanol and an organic acid are uniformly stirred in advance, and then the resulting mixture is added to the previously prepared distilled water including dissolved polyvinyl alcohol. Since the coloring pigment, ethanol and organic acid are uniformly stirred in advance, a much clearer color and excellent coloring may be provided to the lips.

The present invention includes a coloring pigment. As a coloring pigment used in the present invention, a dye changed into a metal compound type which is insoluble in water is preferable. For example, the coloring pigment may be a lake pigment. Due to the lake pigment included in the present invention, a clear color and excellent coloring may be provided to lips. Here, a color of the lake pigment, which is not specifically limited, may be a variety of colors.

In addition, the present invention uses ethanol, to which a coloring pigment is added, instead of wax or oil used in conventional lipsticks or lip glosses.

In addition, the present invention includes an organic acid. Preferably, the present invention may include at least one selected from the group consisting of citric acid, malic acid, tartaric acid and lactic acid. By including the organic acid, nutrients and moisture elements may be further provided and thereby lips become more moist and glossy. In addition, lips may be pigmented and the pigmented color has superior persistency and coloring. Here, as an organic acid, an organic acid not being a salt type is preferable.

In addition, in the present invention, a fragrance may be uniformly stirred with a coloring pigment, ethanol and an organic acid in advance. Here, the fragrance, which is not specifically limited, may be a fragrance element conventionally used in technical fields of the present invention. Preferably, the fragrance may be a water-soluble fragrance element.

[(C) Adjusting pH to 3.0 to 5.5 by Adding Organic Acid]

This step is a step for adjusting a final pH to 3.0 to 5.5 with an organic acid after mixing all materials.

By adjusting pH of the lip pack cosmetic composition for tattooing of the present invention to 3.0 to 5.5, preferably 3.0 to 4.0, a clear color may be provided to the lips and excellent coloring may be anticipated.

The lip pack cosmetic composition for tattooing of the present invention prepared according to the above method includes preferably 0.01 to 0.10 wt % of allantoin, 0.01 to 0.10 wt % of dipotassium glycyrrhizate, 0.5 to 1.0 wt % of butylene glycol, 15.0 to 30.0 wt % of polyvinyl alcohol, 0.01 to 0.20 wt % of a coloring pigment, 1.0 to 5.0% of ethanol (alcohol), 0.1 to 2.0 wt % of an organic acid, 0.05 to 0.50% of a fragrance and 65.0 to 80.0 wt % of distilled water. By including each of the above elements, a color may be efficiently provided to the lips and, at the same time, moist and glossy lips may be expressed due to sufficient moisture supply.

In addition, a formulation of the lip pack cosmetic composition for tattooing of the present invention, which is not specifically limited, is preferably a gel type. By using the gel type composition, it is easy to spread the composition on lips in a proper amount, the spread composition is dried within a short time and thereby forms a thin layer, and the formed layer may be easily removed from the lips.

BRIEF DESCRIPTION OF DRAWINGS

The above and other objects, features and other advantages of the present invention will be more clearly understood from the following detailed description taken in conjunction with the accompanying drawings, in which.

DETAILED DESCRIPTION

EXAMPLES

Hereinafter, the present invention will be described in more detail with reference to the following Examples. The scope of the present invention is not limited to the following Examples and covers modifications of the technical spirit substantially equivalent thereto.

Example 1

Preparation of Lip Pack Cosmetic Composition for Tattooing

After inserting weighted allantoin, dipotassium glycyrrhizate, butylene glycol and distilled water into a container, the mixture was stirred until completely dissolved at 80° C. Subsequently, the resulting mixture was completely dissolved using a homogenizer at 3600 rpm and an Agi-homo mixer (AGI) at 26 rpm while slowly adding polyvinyl alcohol and then cooled at 45° C. Subsequently, a mixture of red color NO. 218 (CI45410:1), ethanol (alcohol), citric acid and a fragrance uniformly stirred was added thereto and then stirred using an Agi-homo mixer (AGI) at 26 rpm while cooling up to 30° C. As a result, a lip pack cosmetic composition was prepared.

Here, the prepared lip pack composition includes 0.05 wt % of allantoin, 0.03 wt % of dipotassium glycyrrhizate, 1.0 wt % of butylene glycol, 18.0 wt % of polyvinyl alcohol, 0.06 wt % of red color NO. 218 (CI45410:1), 3.5% of ethanol (alcohol), 0.35 wt % of citric acid, 0.1% of a fragrance, and 76.91 wt % of distilled water as a solvent.

Comparative Example 1

Preparation of Lip Pack Cosmetic Composition

A lip pack cosmetic composition was prepared in the same manner as in Example 1, except that citric acid was not used and distilled water was used in place of the citric acid in an equal amount.

Comparative Example 2

Preparation of Lip Cosmetic Composition

A lip cosmetic composition was prepared in the same manner as in Example 1, except that polyvinyl alcohol was not used and distilled water was used in place of the polyvinyl alcohol in an equal amount.

Experimental Example 1

Use of Lip Pack Cosmetic Composition for Tattooing

Figure 1:
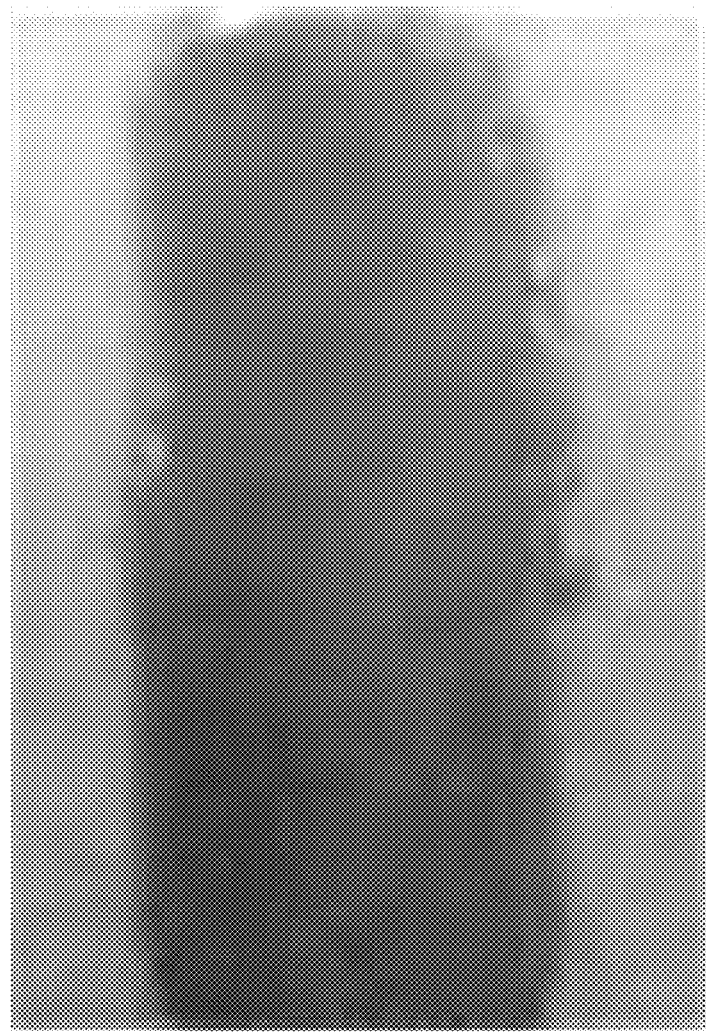
FIG. 1 is an image illustrating a portion of a skin spread with a lip pack cosmetic composition for tattooing.
Figure 2:
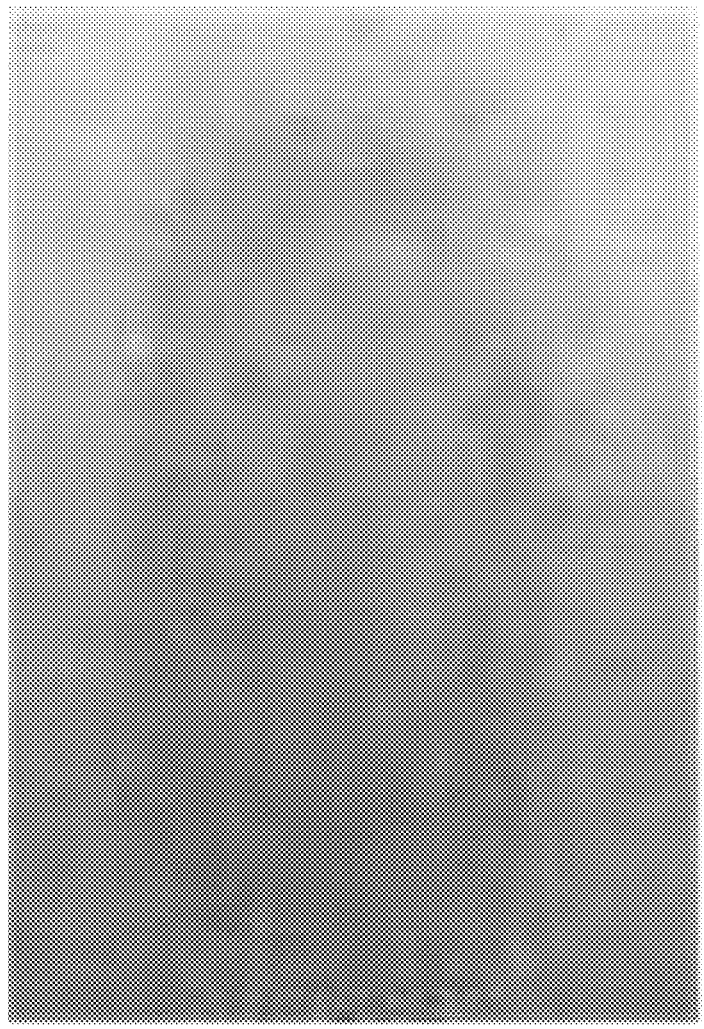
FIG. 2 is an image illustrating a portion of a skin, from which a formed layer (film) is removed, after spreading and drying a lip pack cosmetic composition for tattooing prepared according to Example 1 on a portion of a skin.

A lip pack cosmetic composition prepared according to Example 1 was spread along a lip shape in an amount of 0.1 to 0.2 g as a single dose. Subsequently, when the composition was completely dried after approximately 10 to 15 minutes, a formed layer was slowly removed from lips. Referring to FIGS. 1 and 2, after removing a dried and formed layer, lips were pigmented with an intrinsic color of the product according to the present invention. Therefore, it was confirmed that the lip cosmetic composition for tattooing prepared according to Example 1 may be used as a lip pack cosmetic composition for lip tattooing to provide transient tattoo effects.

Comparative Experimental Example 1

Use of Lip Pack Cosmetic Composition

Figure 3:
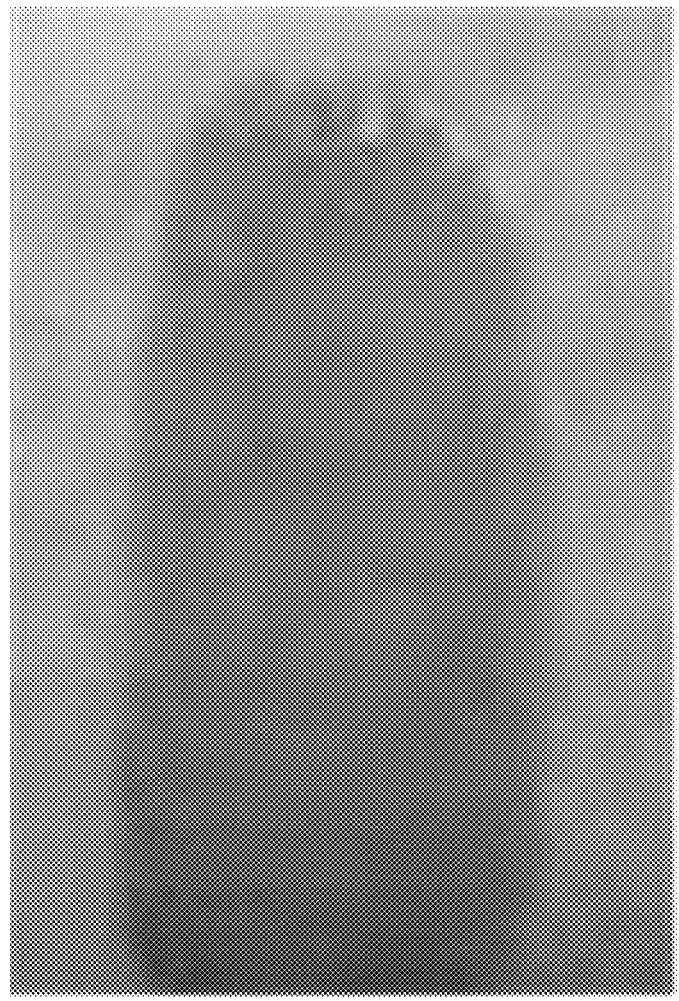
FIG. 3 is an image illustrating a portion of a skin spread with a lip pack cosmetic composition prepared according to Comparative Example 1.
Figure 4:
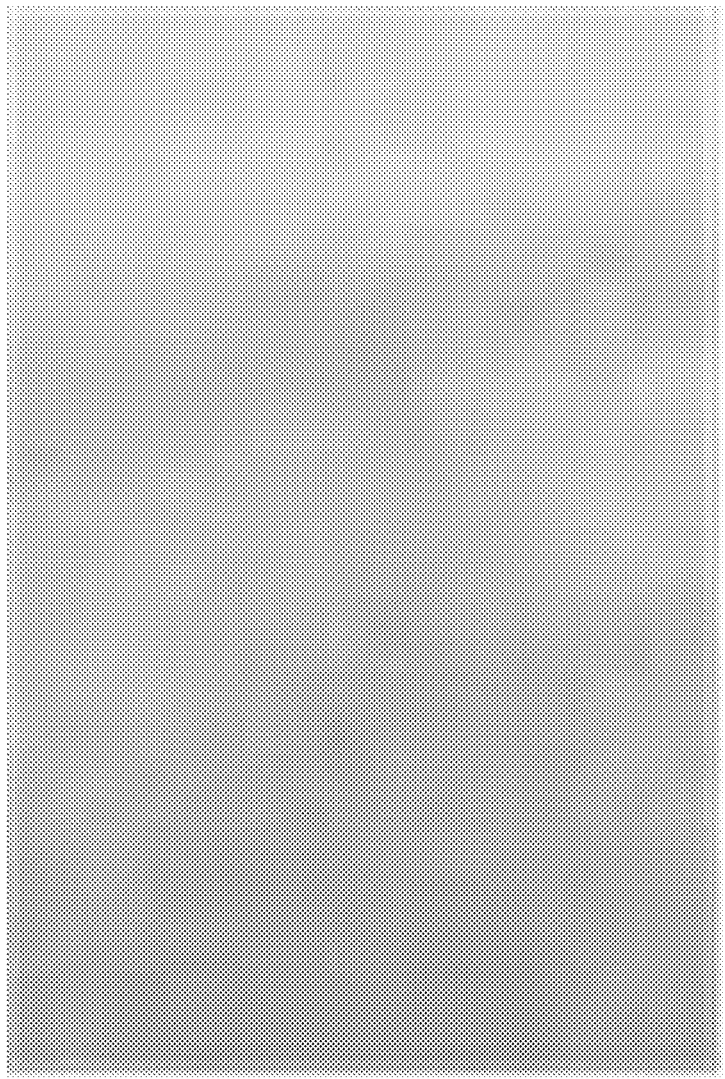
FIG. 4 is an image illustrating a skin, from which a formed layer (film) is removed, after spreading and drying a lip pack cosmetic composition prepared according to Comparative Example 1 on a skin.

A lip pack cosmetic composition prepared according to Comparative Example 1 was spread along a lip shape in an amount of 0.1 to 0.2 g as a single dose. Subsequently, when the composition was completely dried after approximately 10 to 15 minutes, a formed layer was slowly removed from lips. Referring to FIGS. 3 and 4, an intrinsic color of a product was not nearly pigmented on lips, from which a dried and formed layer was removed. Therefore, it was confirmed that the lip pack cosmetic composition prepared according to Comparative Example 1 is not suitable to provide transient tattoo effects.

Comparative Experimental Example 2

Use of Lip Cosmetic Composition

A lip cosmetic composition prepared according to Comparative Example 2 was spread along a lip shape in an amount of 0.1 to 0.2 g as a single dose. After spreading, approximately 10 to 15 minutes passed but a layer was not formed on lips. Therefore, it was confirmed that the lip cosmetic composition of Comparative Example 2 is not usable as a lip pack cosmetic composition.

Comparative Experimental Example 3

Use of Lip Tattoo Sticker

After cutting a commercially available lip tattoo sticker along the sizes and shapes of lips with a scissor, and removing a transparent film from the sticker, a paper portion of the sticker was sufficiently wet while tapping with wet cotton or a wet sponge such that a colored portion of the sticker was attached on lips. When the colored portion was attached to lips, the paper was removed from lips. It was confirmed that color elements were attached on lips after removing the paper.

Usage Example 1

Usage Estimate of Lip Pack Cosmetic Composition for Tattooing

In the Usage Example, usage results of compositions manufactured according to Example 1 and Comparative Experimental Example 3 were compared and evaluated. 30 subjects attended to estimate persistency of lip color, convenience of use, moisturizing ability and convenience of cleansing.

An evaluation score was 1 (very dissatisfied) to 10 (very satisfied). Results are summarized in Table 1 below.

TABLE 1

| | Persistency of lip color | Convenience of use | Moisturizing ability | Convenience of cleansing |
|---|---|---|---|---|
| Example 1 | 9.2 | 9.5 | 9.4 | 9.6 |
| Comparative Experimental Example 3 | 9.6 | 5.4 | 5.3 | 5.7 |

When the lip pack cosmetic composition for tattooing prepared according to Example 1 was spread on lips, a color pigmented on lips was maintained for 12 hours or more, showing excellent persistency. In addition, the lip pack cosmetic composition was not nearly smeared on food containers or foods. Furthermore, anybody may easily use the lip pack cosmetic composition since a formed layer is simply removed from lips after spreading and drying the lip pack cosmetic composition of a gel type on lips. By using the lip pack cosmetic composition, lip moisture was protected and a color pigmented on lips was naturally lost by general cleansing without separate cleansing as a certain time passed.

Meanwhile, when the lip tattoo sticker of Comparative Experimental Example 3 was applied to lips, a color pigmented on lips was maintained for 12 hours or more, showing excellent persistency. However, a use method of the sticker is very inconvenient in that the sticker is cut along the sizes and shapes of lips and, after attaching the sticker to the lips, the stick is tapped with wet cotton or a wet sponge. In addition, by using the stick, lips become dry in a short time and a separate cleansing step for color cosmetics is required to remove the pigmented color. Thus, preference for the stick was very low.

Overall, with the lip pack cosmetic composition for tattooing of the present invention, anybody may easily pigment a color on lips and express transient tattoo effects. At the same time, since lips may be moisturized, moist and glossy lips having a desired color may be expressed. In addition, to remove a color pigmented on lips, a separate cleansing step is not required and the color may be naturally lost when a certain time passed. Therefore, preference for the lip pack cosmetic composition for tattooing of the present invention will be very high.

Example 2

Preparation of Lip Pack Cosmetic Composition for Tattooing

After inserting weighted allantoin, dipotassium glycyrrhizate, butylene glycol and distilled water into a container, the mixture was stirred until completely dissolved at 80° C. Subsequently, the resulting mixture was completely dissolved using a homogenizer (Homo) at 3600 rpm and an Agi-homo mixer (AGI) at 26 rpm while slowly adding polyvinyl alcohol and then cooled to 45° C. Subsequently, a mixture of red color NO. 218 (CI45410:1), ethanol (alcohol), citric acid and a fragrance, which was uniformly stirred, was added thereto and then was stirred using an Agi-homo mixer (AGI) at 26 rpm while cooling to 30° C. Here, pH was adjusted to 3.5 with citric acid. As a result, a lip pack cosmetic composition was prepared.

Here, the prepared lip pack cosmetic composition included 0.05 wt % of allantoin, 0.03 wt % of dipotassium glycyrrhizate, 1.0 wt % of butylene glycol, 18.0 wt % of polyvinyl alcohol, 0.06 wt % of red color NO. 218 (CI45410:1), 3.5% of ethanol (alcohol), 0.3 wt % of citric acid, 0.1% of a fragrance, and 76.96 wt % of distilled water as a solvent.

Example 3

Preparation of Lip Pack Cosmetic Composition for Tattooing

A lip pack cosmetic composition was prepared in the same manner as in Example 2, except that a final pH was adjusted to 4.0 with citric acid. The prepared lip pack cosmetic composition included 0.05 wt % of allantoin, 0.03 wt % of dipotassium glycyrrhizate, 1.0 wt % of butylene glycol, 18.0 wt % of polyvinyl alcohol, 0.06 wt % of red color NO. 218 (CI45410:1), 3.5% of ethanol (alcohol), 0.25 wt % of citric acid, 0.1% of a fragrance, 77.01 wt % of distilled water as a solvent.

Example 4

Preparation of Lip Pack Cosmetic Composition for Tattooing

A lip pack cosmetic composition was prepared in the same manner as in Example 2, except that a final pH was adjusted to 4.5 with citric acid. The prepared lip pack cosmetic composition included 0.05 wt % of allantoin, 0.03 wt % of dipotassium glycyrrhizate, 1.0 wt % of butylene glycol, 18.0 wt % of polyvinyl alcohol, 0.06 wt % of red color NO. 218 (CI45410:1), 3.5% of ethanol (alcohol), 0.20 wt % of citric acid, 0.1% of a fragrance, and 77.06 wt % of distilled water as a solvent.

Example 5

Preparation of Lip Pack Cosmetic Composition for Tattooing

A lip pack cosmetic composition was prepared in the same manner as in Example 2, except that a final pH was adjusted to 5.0 with citric acid. The prepared lip pack cosmetic composition included 0.05 wt % of allantoin, 0.03 wt % of dipotassium glycyrrhizate, 1.0 wt % of butylene glycol, 18.0 wt % of polyvinyl alcohol, 0.06 wt % of red color NO. 218 (CI45410:1), 3.5% of ethanol (alcohol), 0.15 wt % of citric acid, 0.1% of a fragrance, and 77.11 wt % of distilled water as a solvent.

Example 6

Preparation of Lip Pack Cosmetic Composition for Tattooing

A lip pack cosmetic composition was prepared in the same manner as in Example 2, except that a final pH was adjusted to 5.5 with citric acid. The prepared lip pack cosmetic composition included 0.05 wt % of allantoin, 0.03 wt % of dipotassium glycyrrhizate, 1.0 wt % of butylene glycol, 18.0 wt % of polyvinyl alcohol, 0.06 wt % of red color NO. 218 (CI45410:1), 3.5% of ethanol (alcohol), 0.12 wt % of citric acid, 0.1% of a fragrance, and 77.14 wt % of distilled water as a solvent.

Comparative Example 3

Preparation of Lip Pack Cosmetic Composition

A lip pack cosmetic composition was prepared in the same manner as in Example 2, except that citric acid was not used and distilled water was used in place of the citric acid in an equal amount.

Comparative Example 4

Preparation of Lip Cosmetic Composition

A lip cosmetic composition was prepared in the same manner as in Example 2, except that polyvinyl alcohol was not used and distilled water was used in place of the polyvinyl alcohol in an equal amount.

Experimental Examples 2 to 6

Use of Lip Pack Cosmetic Composition for Tattooing

Figure 5:
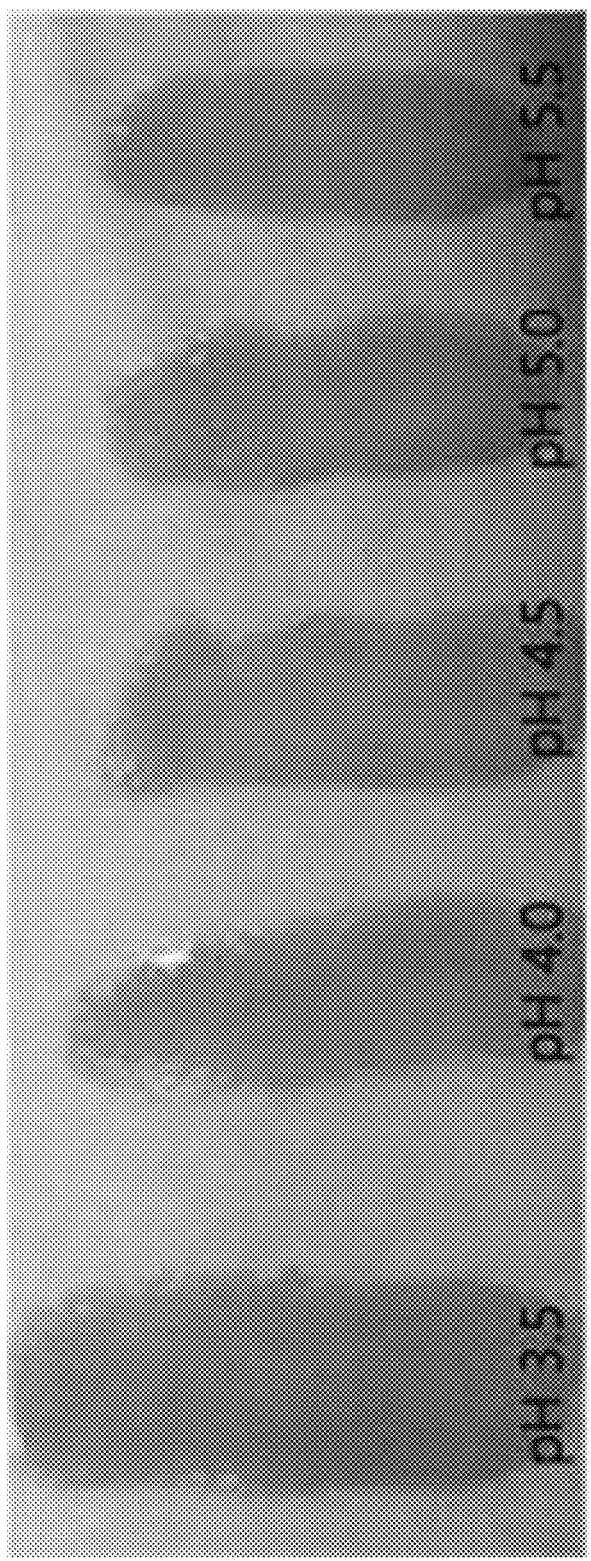
FIG. 5 is an image illustrating a skin spread with a lip pack cosmetic composition for tattooing prepared according to Examples 2 to 6.
Figure 6:
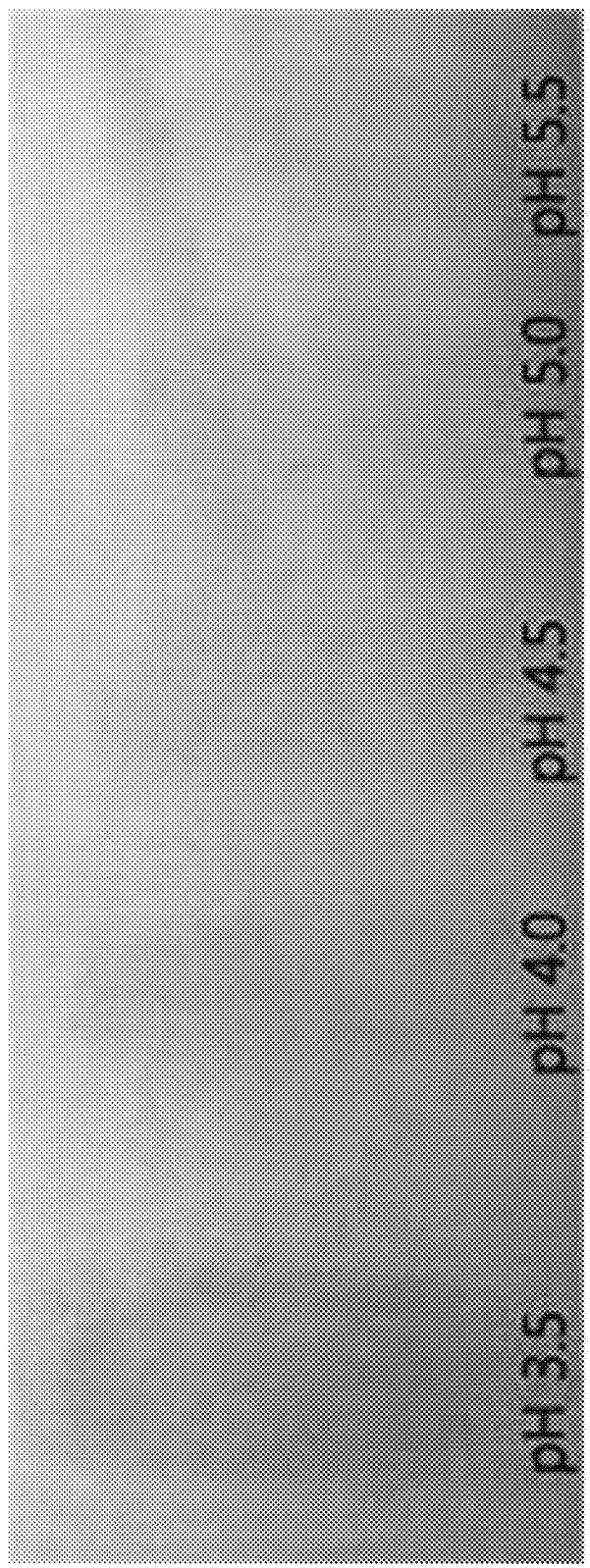
FIG. 6 is an image illustrating a skin, from which a formed layer (film) is removed, after spreading and drying a lip pack cosmetic composition for tattooing prepared according to Examples 2 to 6 on a skin.

Lip pack cosmetic compositions prepared according to Examples 2 to 6 were spread along a lip shape in an amount of 0.1 to 0.2 g as a single dose. Subsequently, when the compositions were completely dried after approximately 10 to 15 minutes, formed layers were slowly removed from lips. Referring to FIGS. 5 and 6, after removing dried and formed layers, lips were pigmented with intrinsic colors of the products according to the present invention. Especially, when pHs was adjusted to 3.5 or 4.0, colors were clear and excellent coloring was observed. Therefore, it was confirmed that the lip cosmetic compositions for tattooing prepared according to Examples 2 to 6 may be used as a lip pack cosmetic composition for lip tattooing to provide transient tattoo effects. Among the compositions, the lip cosmetic compositions for tattooing prepared according to Examples 2 and 3 showed superior effects.

Comparative Experimental Example 3

Use of Lip Pack Cosmetic Composition

Figure 7:
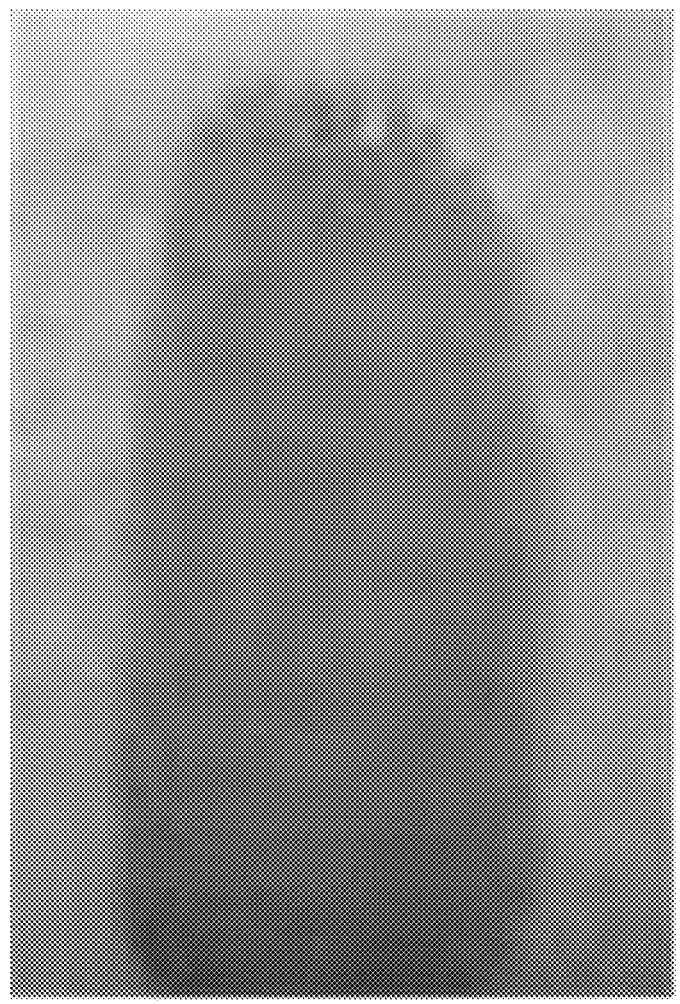
FIG. 7 is an image illustrating a skin spread with a lip pack cosmetic composition prepared according to Comparative Example 3.
Figure 8:
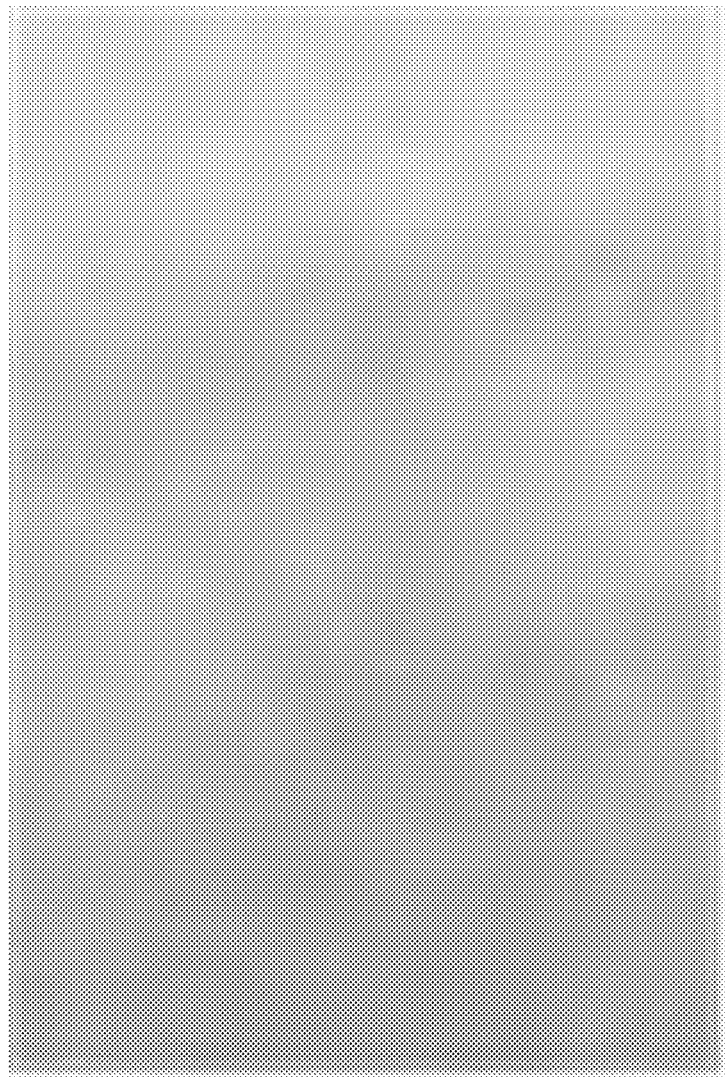
FIG. 8 is an image illustrating a skin, from which a formed layer (film) is removed, after spreading and drying a lip pack cosmetic composition prepared according to Comparative Example 3 on a skin.

A lip pack cosmetic composition prepared according to Comparative Example 3 was spread along a lip shape in an amount of 0.1 to 0.2 g as a single dose. Subsequently, when the composition was completely dried after approximately 10 to 15 minutes, a formed layer was slowly removed from lips. Referring to FIGS. 7 and 8, an intrinsic color of a product was not nearly pigmented on lips, from which a dried and formed layer was removed. Therefore, it was confirmed that the lip pack cosmetic composition prepared according to Comparative Example 3 is not proper to provide transient tattoo effects.

Comparative Experimental Example 4

Use of Lip Cosmetic Composition

A lip cosmetic composition prepared according to Comparative Example 4 was spread along a lip shape in an amount of 0.1 to 0.2 g as a single dose. After spreading, approximately 10 to 15 minutes were passed but a layer was not formed on lips. Therefore, it was confirmed that the lip cosmetic composition of Comparative Example 4 is not used as a lip pack cosmetic composition.

Comparative Experimental Example 5

Use of Lip Tattoo Stickers

After cutting a commercially available lip tattoo stickers along the sizes and shapes of lips with a scissor, and removing transparent film of the sticker, a paper portion of the sticker was sufficiently wetted by tapping with wet cotton or a wet sponge such that a colored portion of the sticker was attached to lips. When the colored portion was attached to the lips, the paper was removed. It was confirmed that color elements were attached on lips after removing the paper.

Usage Example 2

Usage Estimate of Lip Pack Cosmetic Composition for Tattoo

In the Usage Example, usage results of compositions manufactured according to Example 2 and Comparative Experimental Example 5 were compared and evaluated. 30 subjects attended to estimate persistency of lip color, convenience of use, moisturizing ability and convenience of cleansing.

An evaluation score was 1 (very dissatisfied) to 10 (very satisfied). Results are summarized in Table 2 below.

TABLE 2

| | Persistency of lip color | Convenience of use | Moisturizing ability | Convenience of cleansing |
|---|---|---|---|---|
| Example 2 | 9.2 | 9.5 | 9.4 | 9.6 |
| Comparative Experimental Example 5 | 9.6 | 5.4 | 5.3 | 5.7 |

When the lip pack cosmetic composition for tattooing prepared according to Example 2 was spread on lips, a color pigmented on lips was maintained for 12 hours or more, showing excellent persistency. In addition, the lip pack cosmetic composition was not nearly smeared on food containers or foods. Furthermore, anybody may easily use the lip pack cosmetic composition since a formed layer is simply removed from lips after spreading and drying the lip pack cosmetic composition of a gel type on lips. By using the lip pack cosmetic composition, lips were moistly protected and a color pigmented on lips was naturally lost by general cleansing without separate cleansing over time.

Meanwhile, when the lip tattoo sticker prepared according to Comparative Experimental Example 5 was spread on lips, a color pigmented on lips was maintained for 12 hours or more, showing excellent persistency. However, a use method of the sticker is very inconvenient in that the sticker is cut along the sizes and shapes of lips and, after attaching the sticker on lips, the stick is tapped with wet cotton or a wet sponge. In addition, by using the stick, lips become dry in a short time and a separate cleansing step for color cosmetics is required to remove the pigmented color. Thus, preference for the stick was very low.

Overall, with the lip pack cosmetic composition for tattooing of the present invention, anybody may easily pigment a color on lips and express transient tattoo effects. At the same time, since lips may be moisturized, moist and glossy lips having a desired color may be expressed. In addition, to remove a color pigmented on lips, a separate cleansing step is not required and the color may be naturally lost when a certain time passed. Therefore, preference for the lip pack cosmetic composition for tattooing of the present invention will be very high.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method of preparing a lip pack cosmetic composition for tattooing, the method comprising:
   adding polyvinyl alcohol to distilled water to form a solution, and then cooling to 40 to 50° C. ;
   adding a mixture of a coloring pigment, ethanol and an organic acid to the cooled solution of polyvinyl alcohol and distilled water, and then cooling to 25 to 35° C.; and
   adjusting pH to 3.0 to 5.5 by adding an organic acid.

2. The method according to claim 1, wherein at least one skin moisturizer selected from the group consisting of allantoin, dipotassium glycyrrhizate and butylene glycol is dissolved in the distilled water before adding the polyvinyl alcohol.

3. The method according to claim 1, wherein, the mixture of the coloring pigment, the ethanol and the organic acid further comprises a fragrance.

4. The method according to claim 1, wherein, the coloring pigment is a lake pigment.

5. The method according to claim 1, wherein, the organic acid is at least one selected from the group consisting of citric acid, malic acid, tartaric acid and lactic acid.

* * * * *